United States Patent [19]
Gravener et al.

[11] Patent Number: 5,100,042
[45] Date of Patent: Mar. 31, 1992

[54] SURGICAL FASTENER APPARATUS

[75] Inventors: Roy Gravener, Southport; Ernie Aranyi, Easton, both of Conn.; Boris Zvenyatsky, Bronx, N.Y.

[73] Assignee: United States Surgical Corporation, Norwalk, Conn.

[21] Appl. No.: 488,182

[22] Filed: Mar. 5, 1990

[51] Int. Cl.$^5$ .......................................... A61B 17/072
[52] U.S. Cl. .................................. 227/176; 227/178; 227/180; 227/181; 227/19
[58] Field of Search .............. 227/175, 176, 177, 178, 227/180, 181, 21, 19, 120

[56] References Cited

U.S. PATENT DOCUMENTS

| | | | |
|---|---|---|---|
| 3,269,630 | 8/1966 | Fleischer | 227/19 X |
| 4,241,861 | 12/1980 | Fleischer | 227/135 |
| 4,354,628 | 10/1982 | Green | 227/19 |
| 4,422,567 | 12/1983 | Haynes | 227/19 |
| 4,606,345 | 8/1986 | Dorband et al. | 128/334 R |
| 4,665,916 | 5/1987 | Green | 227/19 X |
| 4,715,520 | 12/1987 | Roehr, Jr. et al. | 227/19 |
| 4,728,020 | 3/1988 | Green et al. | 227/19 |
| 4,767,044 | 8/1988 | Green | 227/19 |
| 4,819,853 | 4/1989 | Green | 227/19 |
| 4,881,545 | 11/1989 | Isaacs et al. | 227/178 |
| 4,964,559 | 10/1990 | Deniega et al. | 227/19 X |

FOREIGN PATENT DOCUMENTS 0213817 3/1987 European Pat. Off. .
0216532 4/1987 European Pat. Off. .
0324635 7/1989 European Pat. Off. .

OTHER PUBLICATIONS

"Auto Suture® Poly CS ™ -57 Disposable Surgical Stapler", printed 7/88.
"Auto Suture® Poly CS ™ -57 Disposable Loading Units with LACTOMER® Absorbable Copolymer Staples", printed 7/88.

Primary Examiner—Frank T. Yost
Assistant Examiner—Rinaldi Rada
Attorney, Agent, or Firm—Thomas R. Bremer; Peter G. Dilworth; Rocco S. Barrese

[57] ABSTRACT

An instrument for cutting body tissue and applying a plurality of two part surgical fasteners to the body tissue on each side of the cut. The instrument includes a U-shaped distal portion, and a body having a longitudinal portion for enclosing an axial drive means for pushing fasteners into position in the body tissue. The axial drive means is off-centered from the fastener pushing means in the fastener cartridge at the U-shaped distal portion. A trigger operated diverter is provided with a unique system of force conversion and transmission for converting a single off-centered axial drive force to a uniformly distributed drive force for pushing the fastener pushers, and the knife assembly.

23 Claims, 13 Drawing Sheets

FIG. 7
FIG. 8
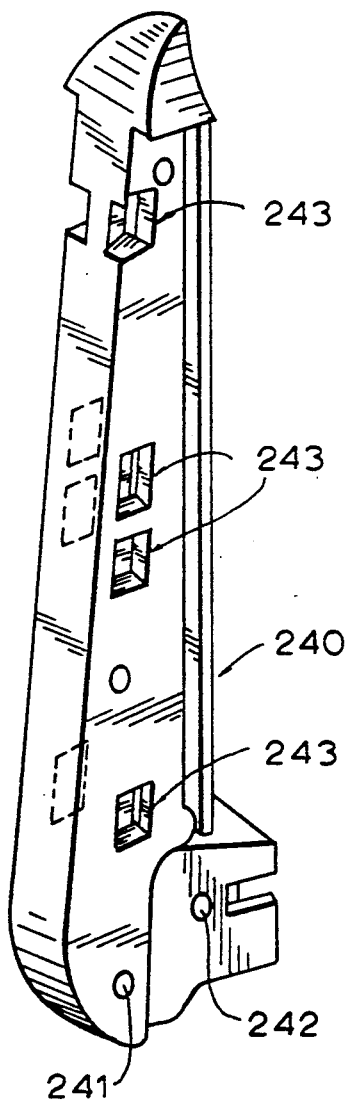
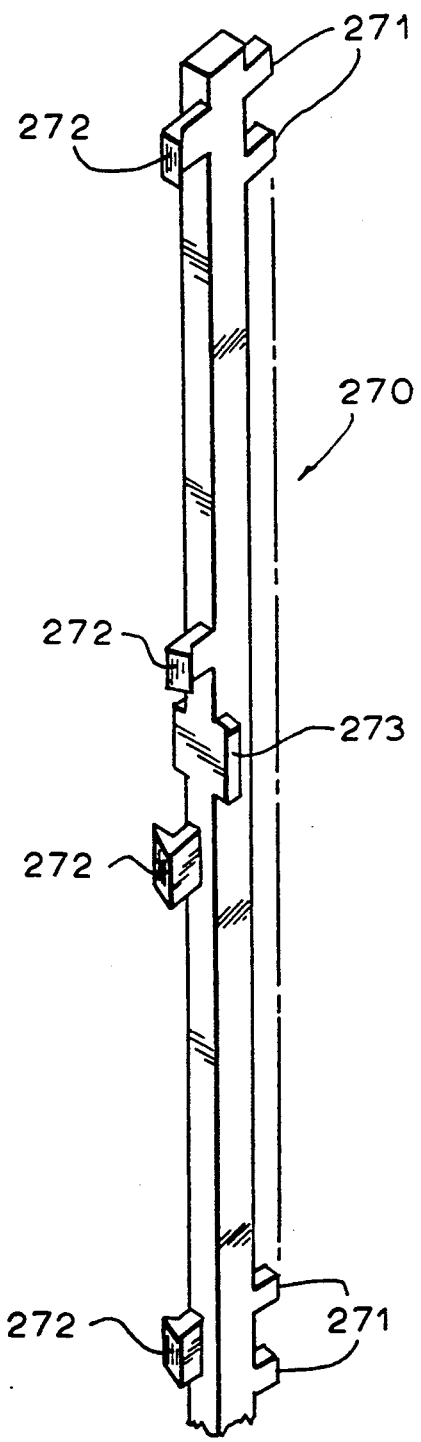

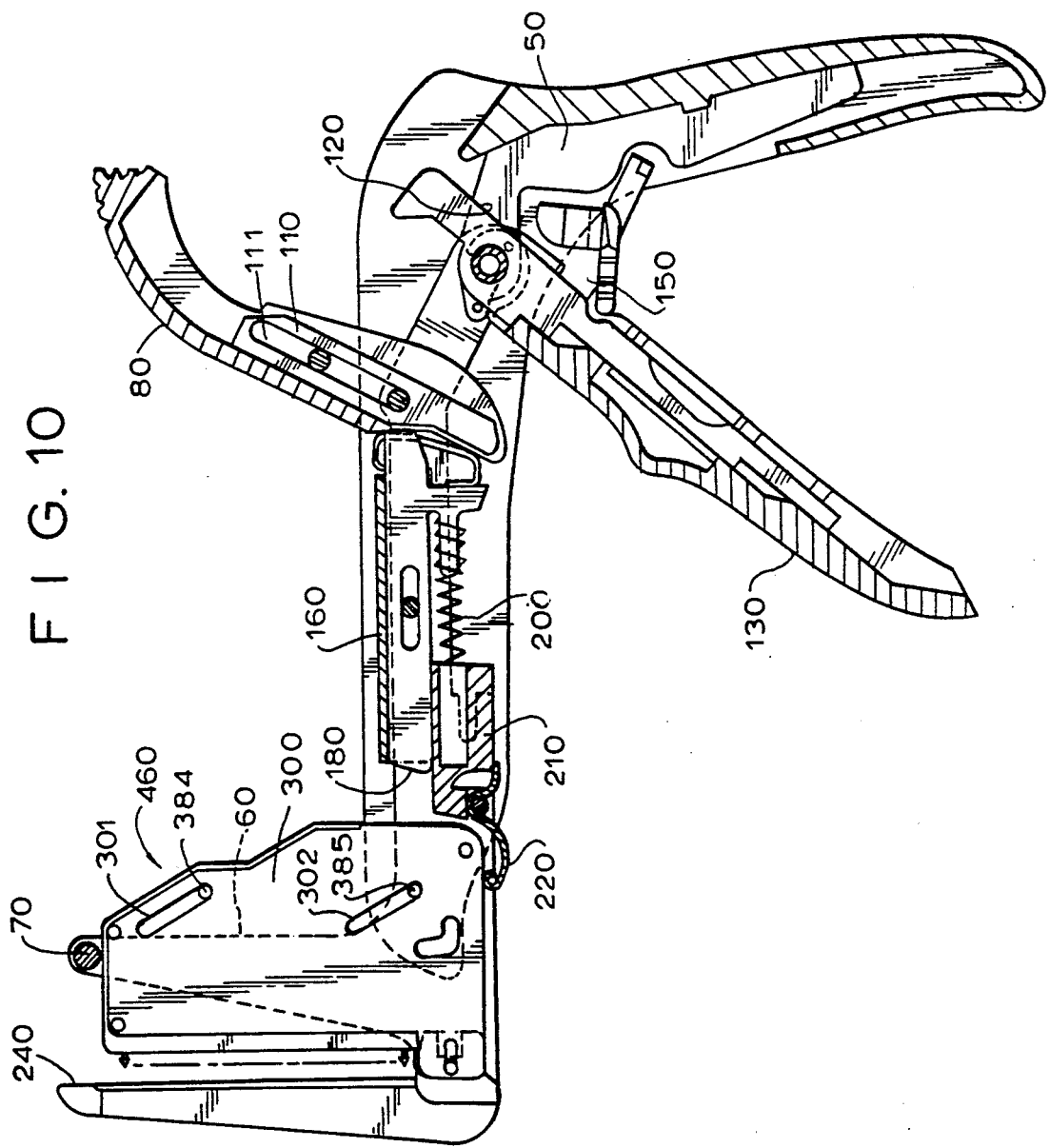

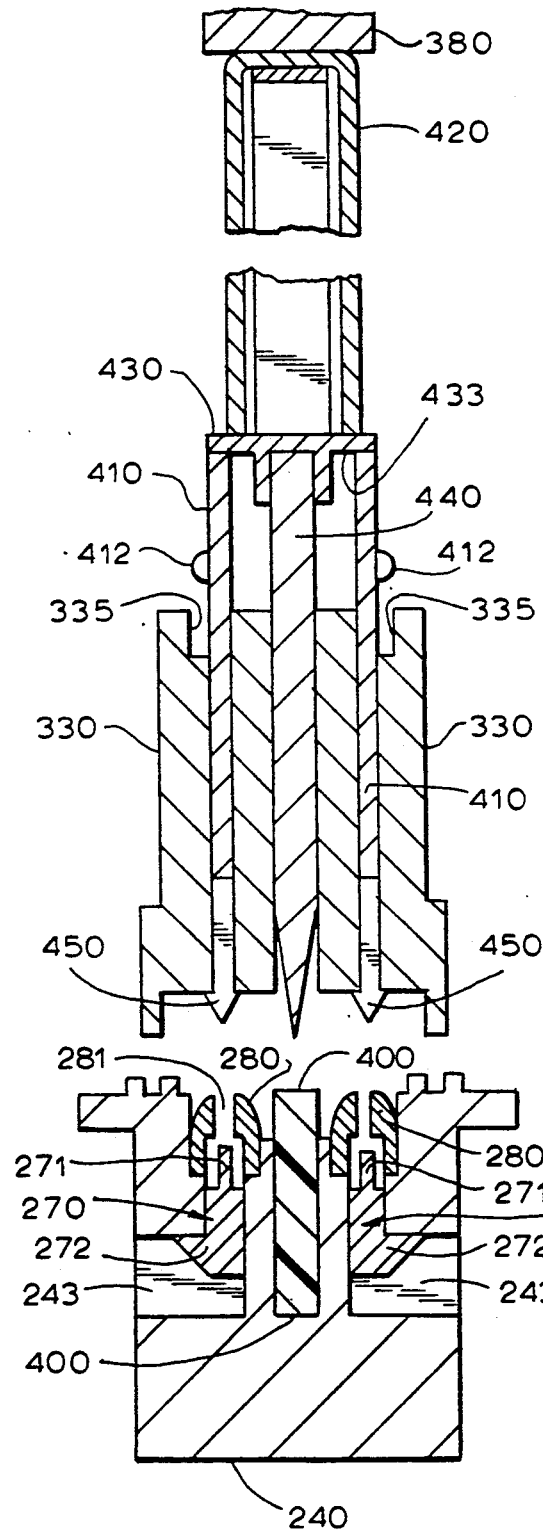
F I G. 14
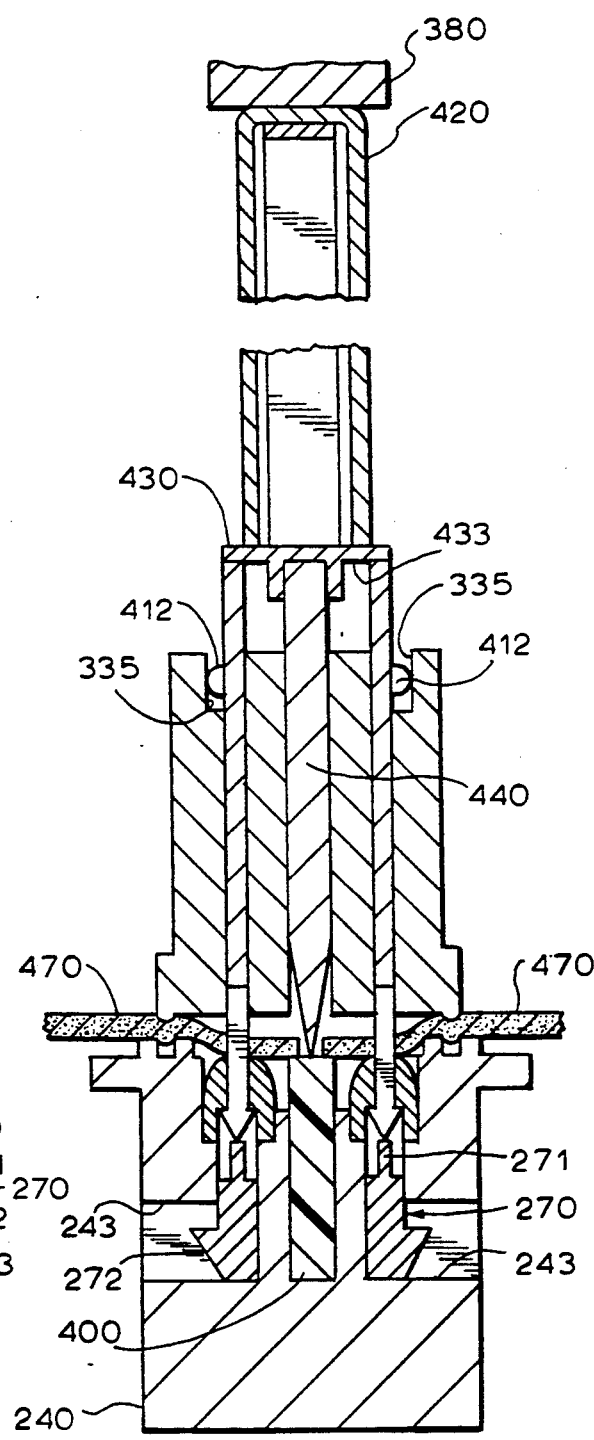
F I G. 15

F I G.16
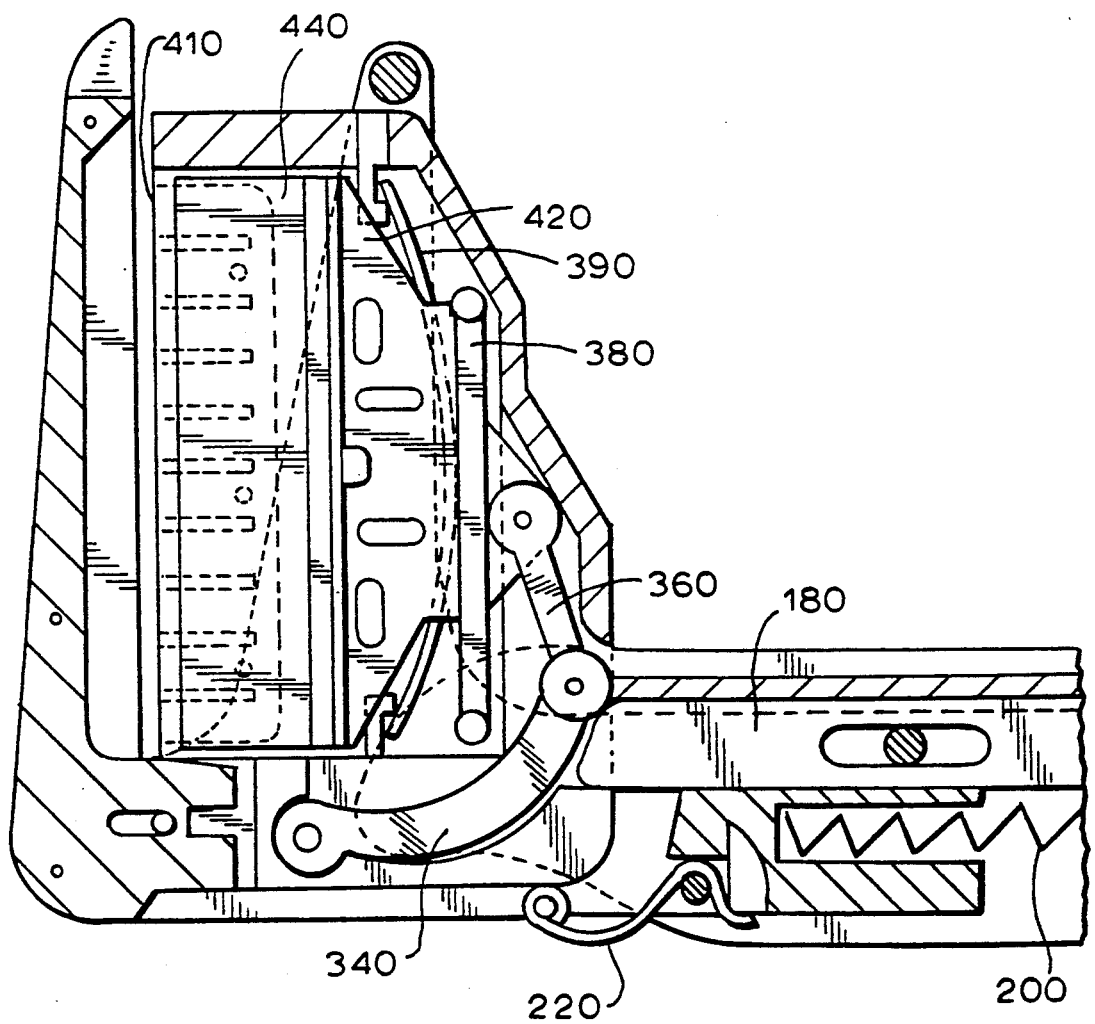

SURGICAL FASTENER APPARATUS

BACKGROUND OF THE INVENTION

1. Field of the Invention

This invention relates to an apparatus for applying a plurality of surgical fasteners to body tissue and more particularly to an apparatus for simultaneously applying a plurality of two part bioabsorbable surgical fasteners.

2. Description of the Prior Art

Surgical fastener applicator apparatus in which surgical fasteners are simultaneously applied to body tissue are known. Typically, these devices include a fastener holder positioned on one side of the tissue to be fastened and an anvil parallel to the fastener holder positioned on the other side of the tissue. Typically, means is provided for linearly translating the fastener holder and the anvil toward one another to clamp the tissue between them. Means in also provided for driving the fasteners from the fastener holder so that the ends of the fasteners pass through the tissue and form finished fasteners as they make contact with the anvil assembly, thereby producing an array of finished fasteners in the tissue.

Also in use are instruments for applying two part fasteners having a fastener portion and a retainer portion. The fastener portion generally has barbed prongs for penetrating body tissue and engaging corresponding openings in the retainer portion. Once engaged, the fastener and retainer are locked together. Such two-part fasteners are usually constructed from bioabsorbable material.

In common use are apparatus in which the fastener holder and anvil are removably mounted in or on an actuator for supporting and actuating the cartridge. The apparatus can be disposed of after a single use or it can be reused for another surgical fastening procedure after cleaning, sterilizing and reloading with a fresh cartridge. Also in use are fully disposable surgical instruments in which the cartridge and actuator are preassembled ready for use and disposed of after only a single use.

U.S. Pat. No. 4,665,916 (Green) describes a surgical fastener apparatus for applying rows of fasteners laterally through hollow body organs such as the thorax, trachea, stomach, uterus or intestines. The cartridge includes an alignment pin which achieves and maintains proper relative positioning of the fastener holder and anvil components thereof. When the fully assembled instrument is actuated, it is positioned in such a way that the body tissue to be fastened is clamped in place between the staple-ejecting surface of the fastener holder and the anvil assembly. The clamping pressure exerted against both sides of the tissue is sufficient to provide effective hemostasis along two linear sites which, upon "firing" of the instrument, receive substantially parallel rows of fasteners on either side of an incision formed by a tissue cutting knife which is also incorporated in the holder. The deployment of the knife is mechanically synchronized to immediately follow the insertion of the fasteners.

U.S. Pat. No. 4,819,853 (Green) discloses a surgical fastener applicator which includes tissue gripping elements provided along the sides of a knife slot to prevent body tissue from pulling away from the fasteners after the latter are positioned in place and the incision is made. Thereafter, clamping pressure is released.

U.S. Pat. No. 4,881,545 (Isaacs et al.) discloses a surgical fastener cartridge possessing an improved body cutting knife assembly. The knife element of the assembly is held in permanent locking engagement with a knife holder.

U.S. Pat. No. 4,767,044 (Green) discloses a fastener applying apparatus including means for preventing all of the fasteners from reaching peak formation force at the same time in order to reduce the maximum force required to operate the apparatus.

U.S. Pat. No. 4,728,020 (Green et al.) discloses an articulated surgical fastener applying apparatus having a linear drive mechanism which is offset from the centerline of movement of the surgical fasteners. The drive force is proximally directed, i.e. it is a pulling force transmitted by a tensioned cable mechanical rather than by a drive rod.

While the prior art instruments, such as those mentioned above, have been serving the needs of the medical community by providing surgeons with quick and simple means to make and/or seal incisions in body tissue, improvements are nevertheless desirable. For example, surgeons prefer to have a greater visibility of the area of tissue upon which they are operating. It should be noted that in the prior art instruments, the drive rod for driving the fastener pushers operates axially and is centered at the rear of the fastener holding cartridge. The longitudinal frame of the instrument, therefore, often interferes with the surgeon's line of sight and obstructs visibility of the operation site.

An off-centered axially moving drive rod would therefore be desirable since it would enable the surgeon to have greater visibility of the operating site. Up to now however, the use of an off-centered drive rod has not been recognized as a solution to the problem. Unlike the cable drive means, the drive rod operates by applying a distally directed, or "pushing" drive force. The central location of the drive rod of the prior art instruments prevents the fastener pushers and the knife, if there is one, from pivoting and jamming within the fastener holding cartridge due to the critical location of the force. Such jamming would occur if the fastener pushers were driven by an off-center force in previously known instruments. Moreover, cable drive means restrict the ability of prior art instruments to be "reset" after initial firing.

The present invention provides such an apparatus in which improved visibility of the operation site is facilitated while avoiding direct off-centered driving force application to the fastener pushing members.

SUMMARY OF THE INVENTION

Apparatus for substantially simultaneously applying a plurality of surgical fasteners to body tissue or the like, which comprises a body having a longitudinal portion enclosing axial drive means, a distal portion thereof defining a tissue reception aperture. Anvil means is positioned at the distal portion of the tissue reception aperture and fastener holding means is pivotally mounted relative to the anvil means adjacent one end portion thereof and defines a space therebetween. The fastener holding means contains a plurality of surgical fasteners arranged in generally parallel rows extending generally transversely to the longitudinal portion and the longitudinal portion is generally offset from the center of the rows of staples. Means is provided for initially advancing the fastener holding means distally at least sufficient to contact body tissue positioned within the aperture, and means is provided for reception of proximally directed user applied force and for translating same to distally directed drive force on the axial drive means generally in alignment with the longitudinal portion. The invention comprises means for translating the distally directed drive force to distally directed staple drive force distributed generally uniformly over the length of the plurality of staples to apply the staples to the body tissue.

In a preferred embodiment, the apparatus disclosed herein for substantially simultaneously applying a plurality of surgical fasteners includes a handle; a trigger means for applying the fasteners; a body with a longitudinal portion enclosing an axial drive means; a U-shaped distal portion; an anvil assembly positioned at the distal leg of the U-shaped distal portion; a fastener holding cartridge pivotally mounted relative to the anvil assembly and adjacent one end of the anvil assembly thereby defining a gap between them, and containing a plurality of surgical fasteners, and optionally including a knife means for cutting body tissue. The apparatus further includes approximating means for actuating the fastener holding cartridge; and a fastener pushing means for substantially simultaneously pushing all of the fasteners from the fastener holding cartridge. The apparatus is characterized in that the axis of the longitudinal portion of the body is in off-center alignment relative to the axial centerline of movement of the fastener pushing means, and said apparatus further includes means for translating an off-centered axial drive force of an evenly distributed driven force across the proximal end of the fastener pushing means.

The U-shaped distal portion of the apparatus is defined by two U-shaped plate portions of frame means mounted in parallel spaced apart relation to each other, the mutually facing surfaces of the plate portions being flat. The two U-shaped plate portions are connected by a spacer pin transversely mounted therebetween at the ends of their respective proximal legs. The said plate portions of the frame means and the spacer pin cooperate so as to align the anvil assembly with the fastener holding cartridge.

The knife means possesses a distally facing elongated surface for contacting the proximal end of the fastener pushing means, the distally facing elongated surface of the knife means abutting and moving said fastener pushing means in response to the distal movement of the axial drive means.

The fastener pushing means includes a pusher plate which is substantially flat on two opposite sides and which has a plurality of fastener-pushing members distally projecting from a back proton, and interference means associated with at least one of the flat sides for frictionally engaging a cooperating surface of the fastener holding cartridge to prevent the fastener pusher plate from moving proximally after it has been moved to its most distal position in response to movement of the axial drive means. The interference means can comprises one or more detents projecting from the side of the pusher plate.

The anvil assembly includes a retainer mounting bar comprising an elongated bar having a plurality of mounting posts projecting transversely from said bar, said posts being frictionally engageable with the retainers for holding said retainers in a fixed position relative to the instrument until said retainers are fully engaged with their respective fasteners.

Although the preferred embodiment described herein pertains to an instrument for substantially simultaneously applying the fasteners, it is also envisioned as being within the scope of the present invention for the instrument to apply the fasteners sequentially. Furthermore, although two-part bioabsorbable surgical fasteners are referred to hereinbelow, instruments for applying other types of surgical fasteners including non-bioabsorbable staples and the like are contemplated as being within the scope of the present invention. Additionally, although the embodiments described hereinbelow are described in conjunction with the fasteners and retainers, it is within the scope of the present invention to provide an instrument in an unloaded condition, such as a reloadable instrument with replaceable fastener and retainer means.

BRIEF DESCRIPTION OF THE DRAWINGS

Preferred embodiments of the invention are described hereinbelow with reference to the drawings wherein:

FIG. 7 is a perspective view of the retainer support arm of the apparatus;

FIG. 8 is a perspective view of the retainer mounting strip of the apparatus;

FIGS. 10, 11, 12 and 13 are elevational views partially cut-away, sequentially illustrating the fastener application with the apparatus of the invention;

FIGS. 14 and 15 are cross-sectional views of the fastener cartridge and anvil assembly, illustrating the operation of the apparatus in prefired and fired conditions, respectively; and FIG. 16 is an elevational cut-away view of the fastener cartridge and anvil assembly after the apparatus has been fired.

DETAILED DESCRIPTION OF THE PREFERRED EMBODIMENTS

Figure 1A:
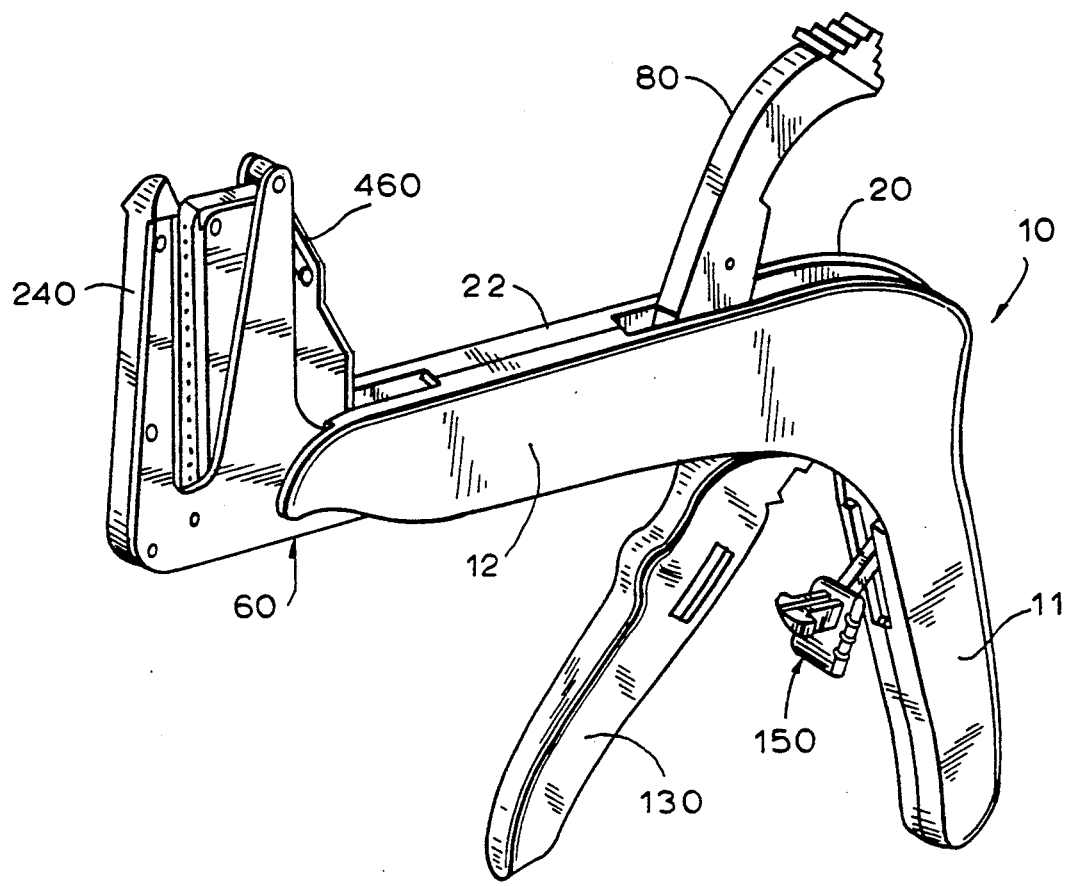
FIG. 1 is a perspective view of the fastener applying apparatus of the present invention.

Referring initially to FIGS. 1 to 4, left and right body portions, 10 and 20 respectively, provide means for housing the actuating mechanism of the invention and also provides means for allowing the user to hold the instrument. Each body portion has a handle portion, 11 and 21 for the left and right body portions respectively, and a longitudinally or axially extending portion 12 and 22, respectively. The body portions also each have internal struts 23 which include recessed portions 23a associated with the internal wall surface of the handle. The struts provide added strength and support. The recessed portions 23a receive and hold the frame extension 50 in a fixed position. Aperture 25 in the right body portion and a corresponding aperture in the left body portion receive trigger pivot pin 140 shown in FIG. 3. Recessed portions 24 and 14 of the right and left body potions form a slot for receiving the pivot arm 151 of safety catch 150.

Figure 3:
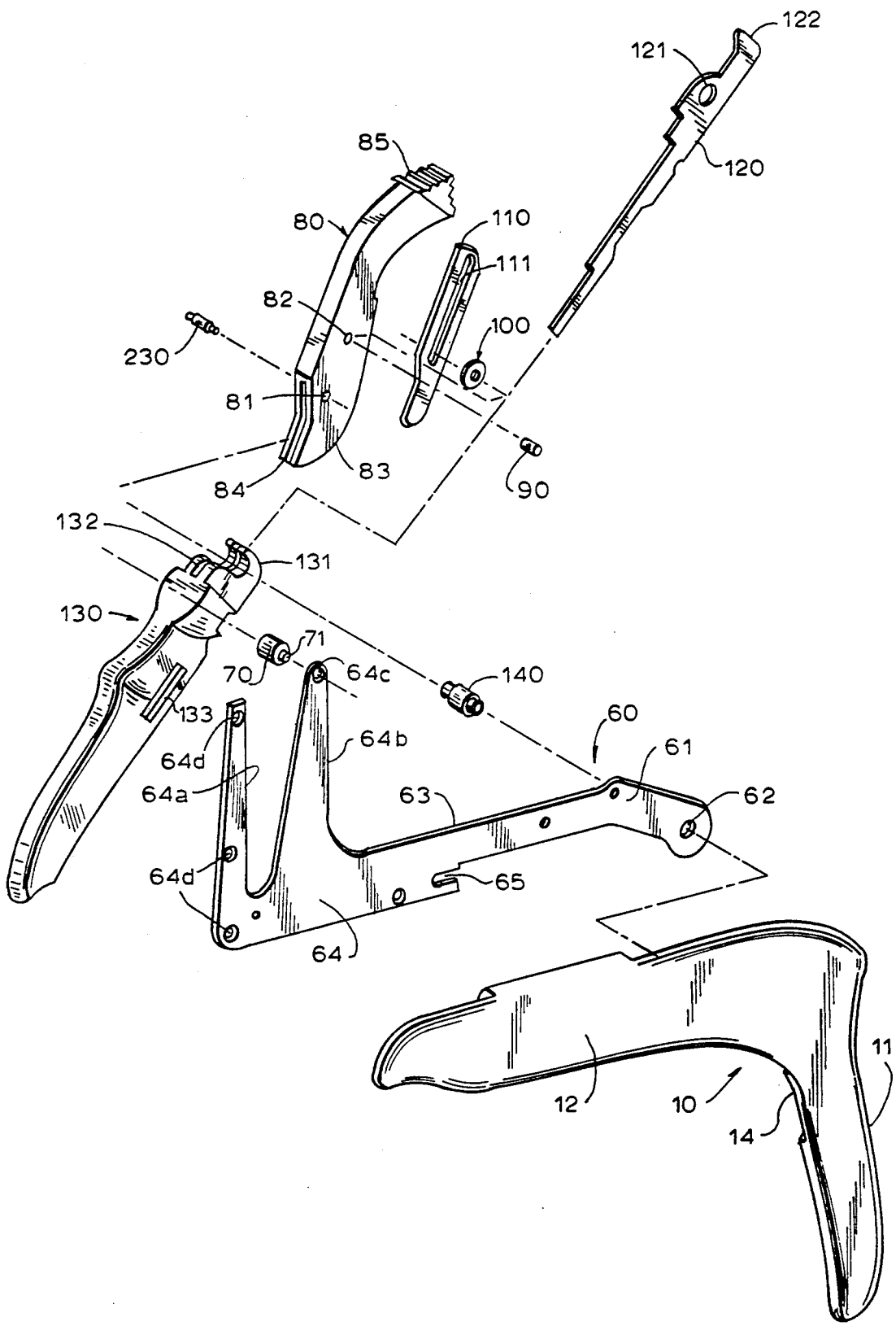
FIGS. 3, 4, 5, and 6 are exploded perspective views of the fastener applying mechanism of the apparatus.

Referring to FIG. 3, left frame 60 is an elongated member having an axially extending longitudinal portion 63; a proximal portion 61 which is inclined from the longitudinal portion and which defines aperture 62 for receiving trigger pivot pin 140; a U-shaped distal portion 64 having a distal leg 64a, a proximal leg 64b, aperture 64c for receiving shoulder rivet 70, and apertures 64d for receiving rivets 250 for mounting to the retainer housing 240 (see FIG. 6); and notch 65 for engaging one of the detents 211 of the spring retainer 210.

Figure 4:
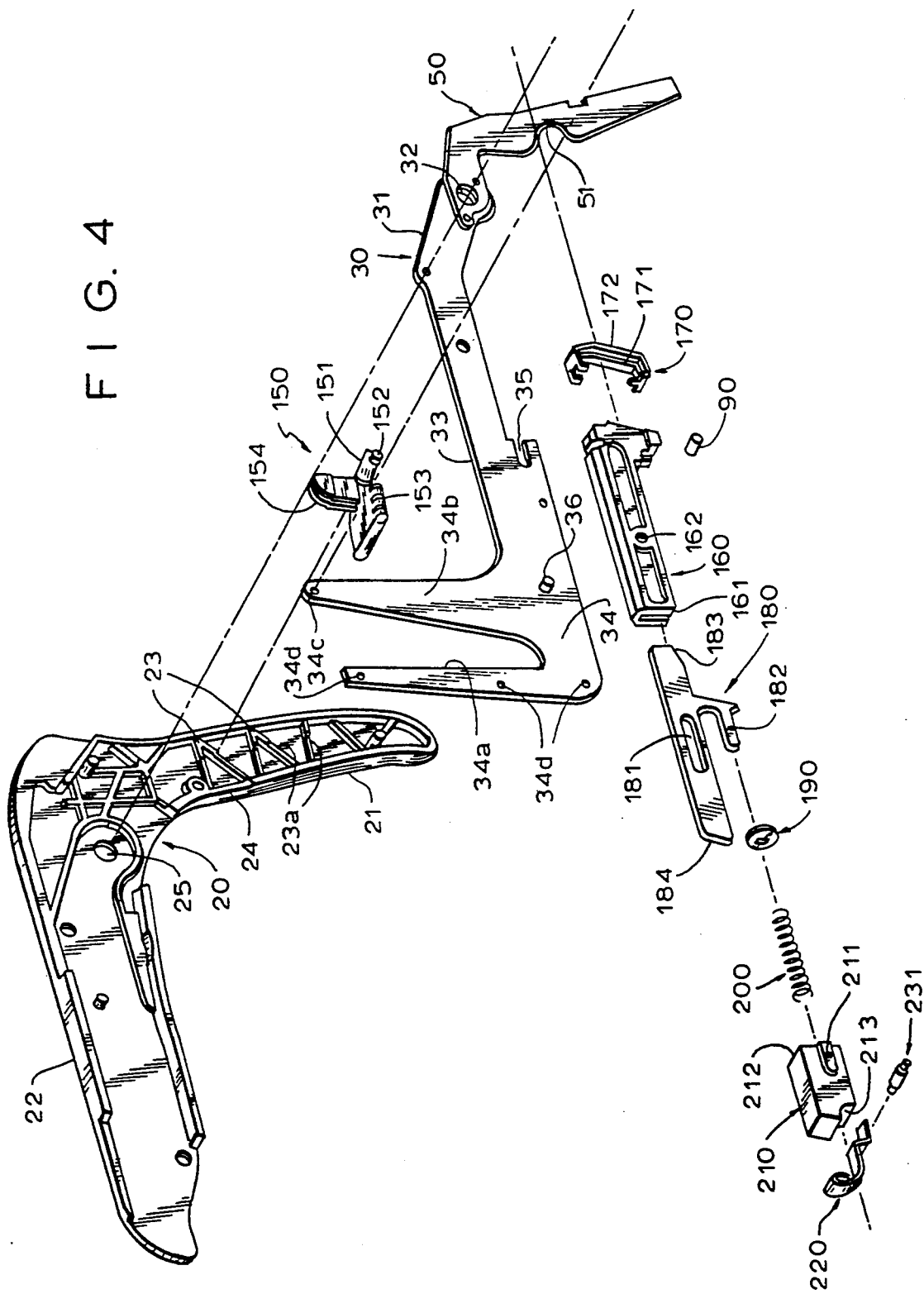
Figure 6:
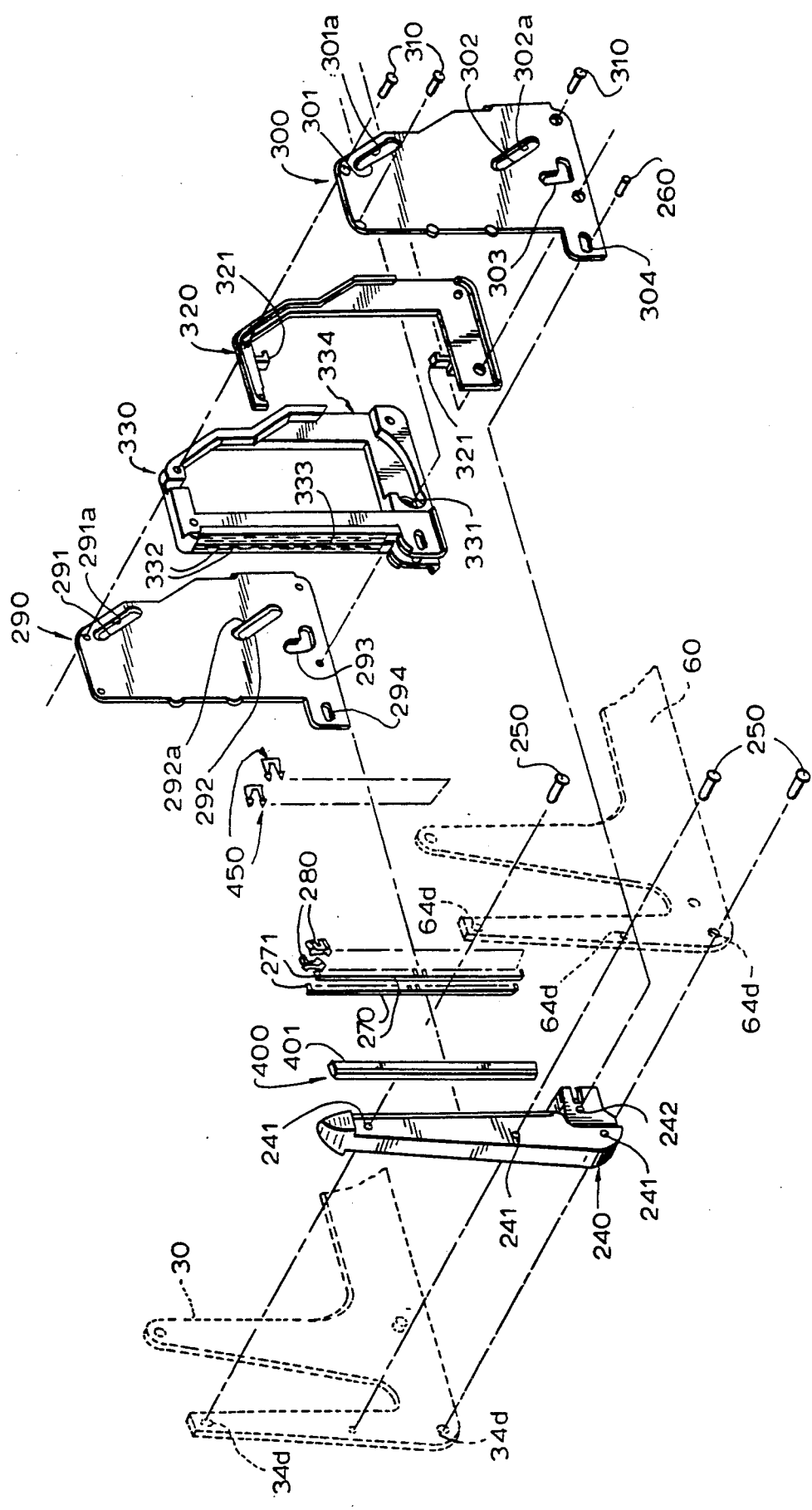

Referring now to FIG. 4, right frame 30 is an elongated member having an axially extending longitudinal portion 33; a proximal portion 31 which is inclined from the longitudinal portion and which possesses an aperture 32 for receiving trigger pivot pin 140; a U-shaped distal portion 34 having a distal leg 34a, a proximal leg 34b, aperture 34c for receiving shoulder rivet 70, and apertures 34d for receiving rivets 250 for mounting to the retainer housing 240 as shown in FIG. 6; and notch 35 for engaging one of the detents 211 of the spring retainer 210 as shown in FIG. 4. Additionally, right frame 30 is fixedly mounted to frame extension 50 such that both have aperture 32 in common. Frame extension 50 has an indentation 51 on its distal edge for accommodating the pivot arm 151 of safety latch 150.

Referring now to FIG. 6, left and right frames 60 and 30, respectively, are mounted in a parallel spaced apart relationship to each other. The distal U-shaped portions define the U-shaped distal end of the instrument. The mutually facing surfaces of the distal portions of the frames are flat thus eliminating intermediate components and facilitating improved component alignment and minimizing dimensional tolerance variations. This is in contrast to prior art instruments in which similarly shaped distal plates possessed inward indentations or jogs to demarcate the distal leg which supported an anvil assembly of lesser width than the fastener holder. In the prior art instruments (see e.g. U.S. Pat. No. 4,665,916) alignment of fastener components and body tissue was provided by a longitudinally mounted alignment pin which pierced the body tissue being fastened. In the present invention alignment is facilitated by the provision of closer tolerances between the flat inner sides of the frames and the fastening holder, by spacer pin 70 which maintains a predetermined distance between the ends of proximal legs 64b and 34b, and through the use of a material of construction for the frames which ensures that the frames will neither deform nor fatigue during use. Preferably, the frames are constructed from stainless steel having a thickness of at least 0.07 inches and preferably of from 0.07 to 0.08 inches. Parallelism and close tolerances are thereby maintained for proper alignment of the fastener holder with the anvil.

Figure 11:
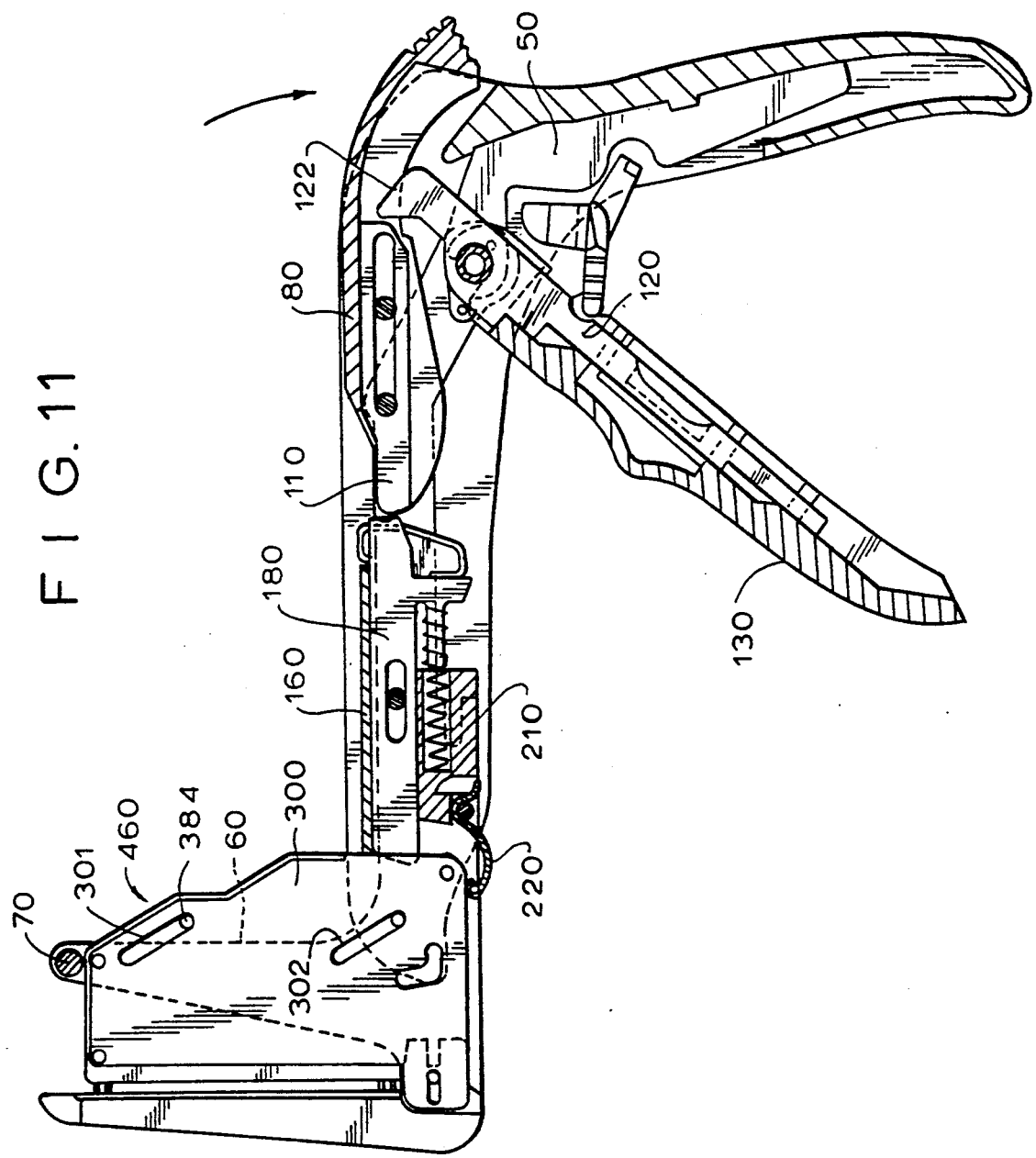

In FIGS. 10 and 11, spacer pin 70 extends laterally between the proximal legs 64b and 34b of the left and right frames, and projections 71 are received into apertures 64c and 34c. Spacer pin 70 spaces the left and right frames apart at a fixed predetermined distance and serves as a guide for the fastener holding cartridge.

Figure 2:
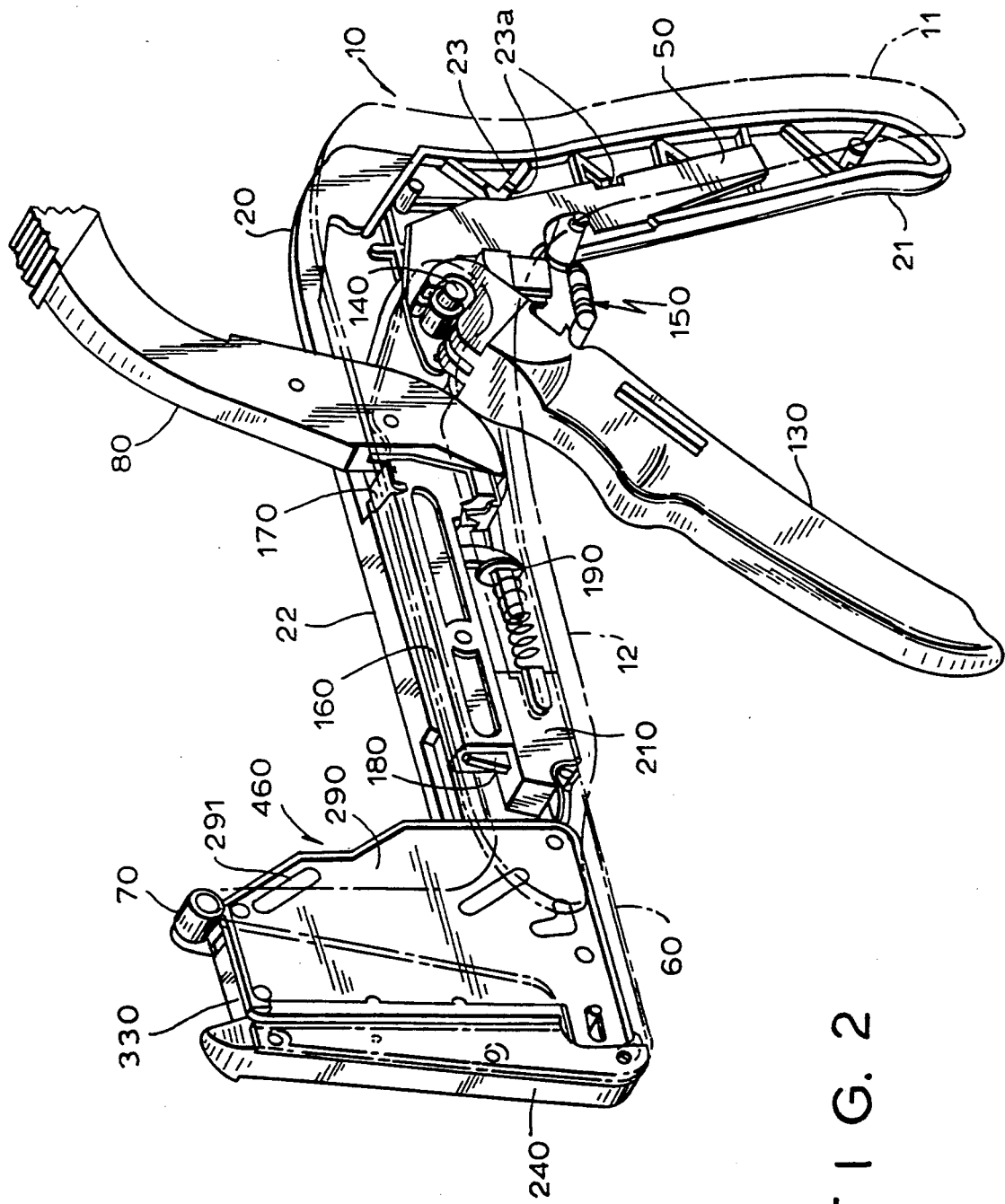
FIG. 2 is a perspective cut-away view of the apparatus of the present invention.

Referring to FIGS. 2 and 3, actuator 80 serves as part of the fastener cartridge actuation means, i.e. approximating means to move the fastener cartridge from a proximal open position such that body tissue can be freely inserted into the gap between the fastener cartridge and the anvil assembly, into a distal closed position wherein it can hold body tissue clamped between it and the anvil assembly, as discussed below. Actuator 80 is a lever pivotally mounted to the left and right body portions 10 and 20 by means of a pin 230 disposed through aperture 81. Aperture 82 receives pin 90 for mounting lever rod 110. Actuator 80 has a forked distal end 83 and a longitudinal central slot 84. Thumb rest 85 is at the proximal end.

Lever rod 110 is an elongated member defining longitudinal central slot 111. Lever rod 110 is slidably mounted within slot 84 of the actuator by means of pin 90 disposed through aperture 82, washer 100 and slot 111.

Trigger 130 is an elongated lever arm having a forked end with curved hook-like members 131 shown in FIG. 3. Central slot 132 extends longitudinally along the underside of the trigger 130. Side slots 133 are provided for engaging the snap prongs 154 of the safety catch 150. Central slot 132 is provided in trigger 130 for receiving trigger insert 120, which is mounted therein. Trigger insert 120 has an aperture 121 which is aligned with the curved hook-like members 131 such that trigger pivot pin 140 is received therethrough. Trigger insert 120 has an end with projection 122 for contacting the proximal end of lever rod 110.

Referring once again to FIGS. 2 and 3, trigger pivot pin 140 is transversely mounted with left and right ends fixed respectively in apertures 25 in the interior surfaces of the left and right body portions 10 and 20, and is disposed respectively through apertures 62, 121, and 32, of the left frame, trigger insert and right frame.

Referring to FIG. 4, safety catch 150 includes panel 153, and projections 152 for pivotally mounting into corresponding apertures in the left and right body portions.

Referring to FIGS. 4, 10 and 11, clamp 160 is an elongated member with longitudinal central slot 161. Cap 170 is mounted on the proximal end of clamp 160 with vertical slot 171 of the cap being aligned with longitudinal slot 161 of the clamp to permit passage therethrough of lever 110. Cap 170 preferably has a sloped proximal surface 172 for being contacted by the forked end 83 of the actuator. Clamp 160 has a transversely extending aperture 162 for receiving clamp pin 90.

Thrust bar 180 is an elongated member which is slidably mounted within slot 161 of the clamp. Thrust bar 180 has a longitudinal slot 181 through which clamp pin 90 is disposed. Proximal end 183 is for contacting the distal end of lever 110. Distal edge 184 is for contacting the cam assembly discussed below and is preferably inclined to facilitate camming action between it and link 340. Thrust bar 180 has a distally projecting post 182 for mounting a washer 190, and coiled spring 200.

Spring retainer 210 is a block shaped piece having longitudinally extending detents 211 for engaging slots 65 and 35 in the left and right frames. The proximal ends 212 serves as a backstop for spring 2200 such that spring 200 biases the slidable thrust bar 180 in the proximal direction. The distal end has a curved portion 213 for receiving a leaf spring 220.

Retainer pin 231 extends transversely across the underside of the leaf spring 220 and is fixed at its ends in corresponding apertures in the body portions. Retainer pin 231 maintains the spring 220 in a fixed position.

Figure 5:
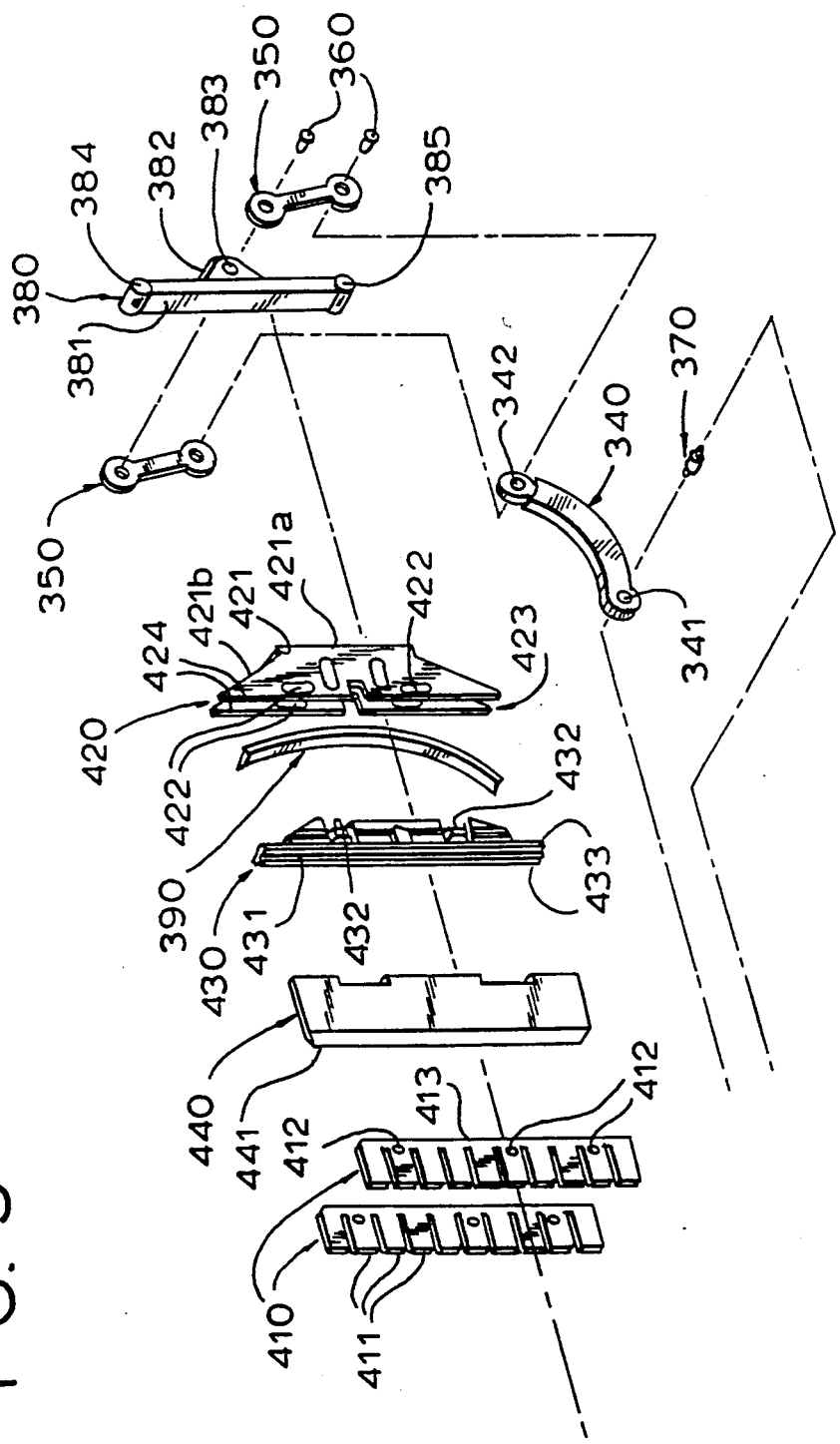

Referring additionally to FIGS. 5 and 6, the fastener holder 460 of the present invention is an assembly which includes several unique features.

The cam assembly, which is housed within the fastener holder 460, is a non-torquing force diverter comprising an assembly of links and a cam plate which converts the off-centered axial drive force to a balanced linear drive force uniformly distributed across the proximal end of the knife blade assembly. With such means for providing this conversion, the need to provide an off-centered drive force directly to the knife assembly is avoided. Such last mentioned force application method would result in unbalanced force and unwanted torque which would pivot and jam the knife and fastener pushers. Moreover, in the present invention, force transmissions and conversions are provided through compression members thereby facilitating definitive and accurate force transmission and conversion. Furthermore, tension cables or the like as utilized in prior developments are avoided.

Referring to FIG. 5, the cam assembly includes curved link 340 having a distal end pivotally mounted in socket 331 in the fastener cartridge 330 by means of pin 370 disposed through aperture 341. The proximal end of link 340 is pivotally attached by a pin 360 disposed through aperture 342 to one end of an intermediate link 350. The other end of the intermediate link 350 is pivotally attached by a pin 360 to cam bar 380. Cam bar 380 has a flat distal camming surface 381, a rear projection 382 with aperture 383 for receiving a pivot pin 360, and upper and lower bolts 384 and 385 which project into and ride along the inclined slots 291, 292, 301, and 302 of the right and left side plates. The flat distal camming surface 381 of the cam bar is for contacting the proximal surface 421a of the back of the blade channel 420.

The movement of the cam bar has a vector component linearly aligned with the path of movement of the fastener pushers 410, knife 440, and blade channel 420. Unaligned components of motion are not transmitted to the blade channel 420 because the cam bar's distal surface 381 remains in a perpendicular orientation relative to the center line of movement of the fastener pushers 410 and blade channel 420, and because the camming surface 381 is slidable relative to proximal surface 421a.

Referring once again to FIG. 5, the knife blade assembly, also housed within the fastener holder 460, includes blade channel 420, leaf spring 390, blade holder 430, and knife blade 440.

Blade channel 420 has two parallel dovetail shaped portions 424 projecting distally from a back portion 421. The dovetail portions define apertures 422 for engaging projections 432 of the blade holder 430. Together, dovetail portions 424 define a channel 423 in which leaf spring 390 is located. The back portion 421 has a proximal surface 421a for contacting the distal camming surface 381 of the cam bar, and a distal surface 421b which is contacted by leaf spring 390.

Curved leaf spring 390 is located between the blade holder 430 and the blade channel 420. Its ends are retained by inwardly projecting stubs 321 of the cartridge cap 320. Spring 390 contacts the distal surface 421b of the back of the blade channel 420, thereby biasing the blade channel 420 proximally.

The distal end of blade holder 4320 has a slot 431 for mounting a knife blade 440. Projections 432 on the side of the blade holder are mounting fixtures received into apertures 422 of the blade channel.

Knife blade 440 has a sharp distal edge 441 for cutting body tissue. The proximal edge of blade holder 430 shown in FIG. 5 is mounted in slot 431 of the blade holder.

Referring once again to FIG. 5, cartridge pushers 410 are substantially flat strips having distal pointing finger-like projections 411 for pushing the fasteners through slots 332, and out of the cartridge 330 into engagement with their respective retainers 280 in the anvil assembly. At least one side of each pusher possesses an interference means, such as one or more detents 412, which frictionally engage the surface 335 of the corresponding slot in the fastener cartridge 330 in which the pusher slides. (See FIG. 15.) These detents advantageously prevent the pushers from retracting once they have been moved to their most distal position, thereby preventing the fasteners from migrating or deflecting back into slots 332. Such migration or deflection, if unimpeded, may result in non-engagement of the fastener with its corresponding retainer. The proximal edges 413 are contacted by surfaces 433 of the blade holder such that when the blade holder is moved distally, surfaces 433 urge the fastener pushers 410 towards the distal direction.

Fastener holder 460 also comprises cartridge 330 having a plurality of fastener slots 332, a knife slot 333, a rear slot 334 through which the distal end 184 of the thrust bar enters, and socket 331 for retaining distal end 341 of the curved link.

Cartridge cap 320, which is mounted to cartridge 330, has inwardly projecting stubs 321 for retaining the ends of the leaf spring 390.

Left and right side plates 330 and 290 respectively each have two inclined slots (301 and 302 in side plate 300; 291 and 292 in side plate 290) for retaining the bolts 384 and 385, which are slidably received therein. Said slots are defined by guide surfaces (301a, 302a, 291a, 292a, respectively) which contact the circumferential surfaces of the respective ends of the bolts disposed therethrough and restrain the movement of the bolts to a predetermined linear path. The width of the slots 301, 302, 291, and 292 closely match the width of the respective bolts 384 and 385 while leaving enough clearance for free sliding of the bolts. Slots 304 and 294 receive cartridge pivot pin 260, which pivotally mounts the fastener holder 460 to the frame. Slots 303 and 293 receive bosses 36 of the inner sides of the respective frames. Pins 310 are disposed respectively through apertures in the left side plate 300, the cartridge cap 320, the cartridge 330, and the right side plate 290.

The anvil assembly comprises retainer support arm 240, anvil block 400, retainer holding strips 270, and retainers 280. Arm 240 is mounted between the distal arms 64a and 34a of the frames by means of pins 250 disposed through corresponding apertures 241 in the arm 240, and apertures 64d and 34d in the frames. Aperture 242 in the arm receives cartridge pivot pin 260. In other embodiments, the anvil assembly can include a means for replacing retainers (for example in reusable/reloadable instruments), or crimping means (for example, with metal staples).

Figure 9:
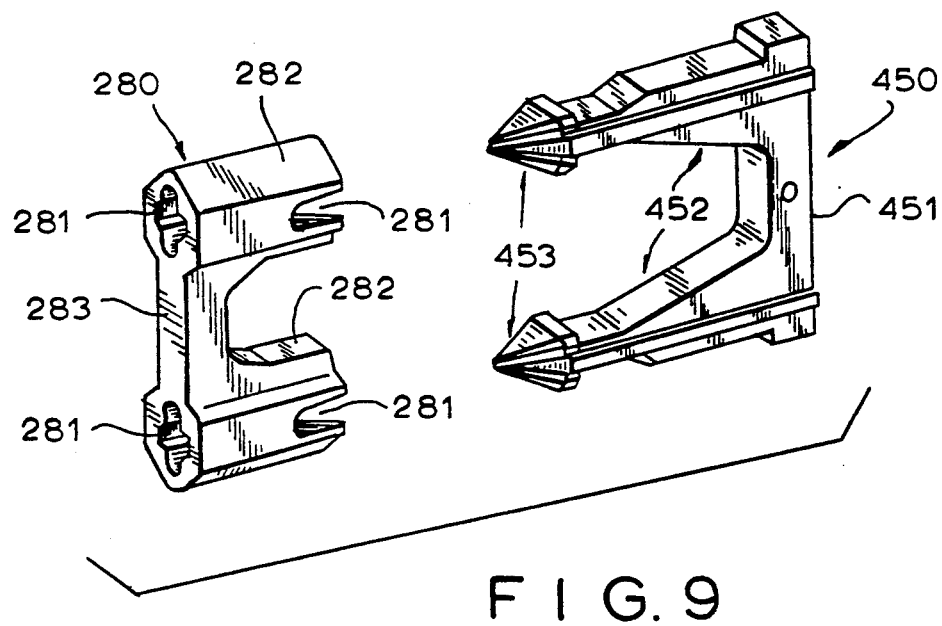
FIG. 9 is an enlarged perspective view of the two part surgical fastener which can be applied to body tissue by means of the apparatus of the present invention.

Referring additionally now to FIG. 9, two-part bioabsorbable surgical fasteners useful in the present invention generally comprise a fastener portion 450 having a backspan 451, and prongs 452 with barbs 453 at the tips thereof. The fasteners are initially located in slots 332 of the cartridge. When the pusher members 410 are distally moved, the finger-like projections 411 each contact the backspan 451 of a fastener 450, thereby moving it through and out of its respective slot 332. The retainer portion 280 of the two-part fastener comprises a base 283 with columnar members 282 having apertures 281 for receiving the barbed prongs 452 of the fastener. Once engaged, the fastener and the retainer lock together, hence the desirability of constructing them of bioabsorbable material such as polyglycolide, polylactide or copolymers thereof for suturing body tissue.

Referring again to FIG. 6 and additionally to FIGS. 7 and 8, retainers 280 are preferably mounted on retainer mounting strips 270 in arm member 240 such that each retainer is aligned with a corresponding fastener portion in the respective fastener slots 332. Mounting strip 270 includes a plurality of mounting posts 271 each of which frictionally engages a respective aperture 281 of the retainer. Mounting strip 270 also includes projections 273 which ride in a corresponding slot in retainer support arm 240, and which serve as a limiter to prevent lateral sliding of the mounting strip. Hook-shaped catches 272 snap into windows 243 of the retainer support arm 240 thereby preventing the retainer mounting strips 270 from dropping out of the support arm 240. Mounting strip 270 is thus adapted to be loaded with retainers prior to its introduction into retainer support arm 240. This external retainer-loading feature of mounting strip 270 is particularly advantageous because the retainers are typically quite small, e.g., about 0.2 inches in length, and are therefore difficult to handle. Mounting strip 270 permits retainers to be conveniently mounted onto mounting posts 271 and then the entire mounted assembly is easily snapped into retainer support arm 240. Reloading of mounting strip 270 is also facilitated by simply removing the mounting strip from the retainer support arm, mounting fresh retainers, and repositioning within retainer support arm 240.

Preferably, at least two rows of retainers 280 are mounted in an arm 240. The rows are separated by an anvil block 400 which provides a means for contacting body tissue and providing a backstop surface 401 for the cutting edge 441 of the knife. When the barbed prongs 452 enter the top of the column members 282, the posts 271 are pushed out of the opposite end of the apertures 281 by the entering barb 453, and thereby disengage the retainer 280, releasing it from the anvil assembly.

Referring to FIGS. 10 to 13, the instrument is initially in the open and unfired condition illustrated in FIG. 10. For use in surgical operations it is positioned by the surgeon such that the body tissue to be fastened is located in the U-shaped distal portion between the jaws of the instrument, i.e. in the gap between the fastener holder 460 and the anvil assembly. The surgeon then actuates the instrument: by pivoting actuator lever 80 down (i.e. clockwise as shown) from the position shown in FIG. 10 to the position shown in FIG. 11. By this movement, the fastener holder 460 will move distally to a closed position wherein it contacts the body tissue (not shown) to secure the body tissue in a fixed position. Moving the actuator lever 80 down also moves the clamp 160 forward and aligns lever 110 along the longitudinal axis of the instrument. The distal end of clamp 160 contacts the fastener cartridge 460 and moves it from the open position to a closed position. It should be noted that until lever 110 is aligned, the fasteners cannot be fired.

The instrument at this point is in the condition illustrated by FIGS. 11 and 14. The next step for the surgeon is to release the safety catch 150 by pivoting it down (counter-clockwise as shown), thereby putting the instrument in a "ready to fire" condition.

To fire the instrument, the surgeon pivots the trigger lever 130 (counter-clockwise as shown) by manual application of a proximally directed force. This movement, in turn, pivots trigger insert 120 and converts the proximally directed force to a distally directed force such that portion 122 moves lever 110 distally. Lever 110 pushes the thrust bar 180 distally, and thrust bar 180 presses on link 340. This motion is transferred by link 350 to cam bar 380. Cam bar 380 has a path of movement defined by slots 291, 292, 301, and 302, all of which are aligned in the same predetermined direction. The vector components of motion of the cam bar include a vector component linearly aligned with the center line of motion of the knife assembly and fastener pushers 410. Although the path of movement of the cam bar 380 is in a directional line which is at an angle from the center line of movement of the knife assembly and fastener pushers, it does not exert pivotal or torquing motion of these parts. Torque is avoided because the cam bar is constrained to an orientation perpendicular to that of the above mentioned center line of movement by the relatively close fit of the bolts 384 and 385 within their respective guide slots 291, 292, 301, and 302, and because the distal surface 381 of the cam bar will slide across surface 421a, thereby preventing unaligned vector components of cam bar motion from being transmitted to blade channel 420. Thus the force conversion and transmission is positive and accurate due to the precise movement of compressor members in engagement with each other.

The blade channel 420 is moved forward by the cam bar 380 and surface 433 pushes the fastener pushers distally, thereby driving the fasteners out of the slots, and into the retainers. Detents 412 on the fastener pushers 410 frictionally engage the surface 335 of their respective slots in cartridge 330. This frictional engagement prevents the fastener pushers from returning to their proximal position after they have been moved to their distal position. Knife blade 440 is moved distally through slot 333 thereby cutting any body tissue 470 (shown in FIG. 15) between the knife and the anvil block 400 which the knife edge 441 impinges. The instrument thereby creates an incision into body tissue which is sealed by a row of fasteners on each side.

The prongs 154 of the safety catch snap into locking engagement with slots 133 of the trigger and thereby prevent inadvertent firing of an unloaded instrument.

Figure 12:
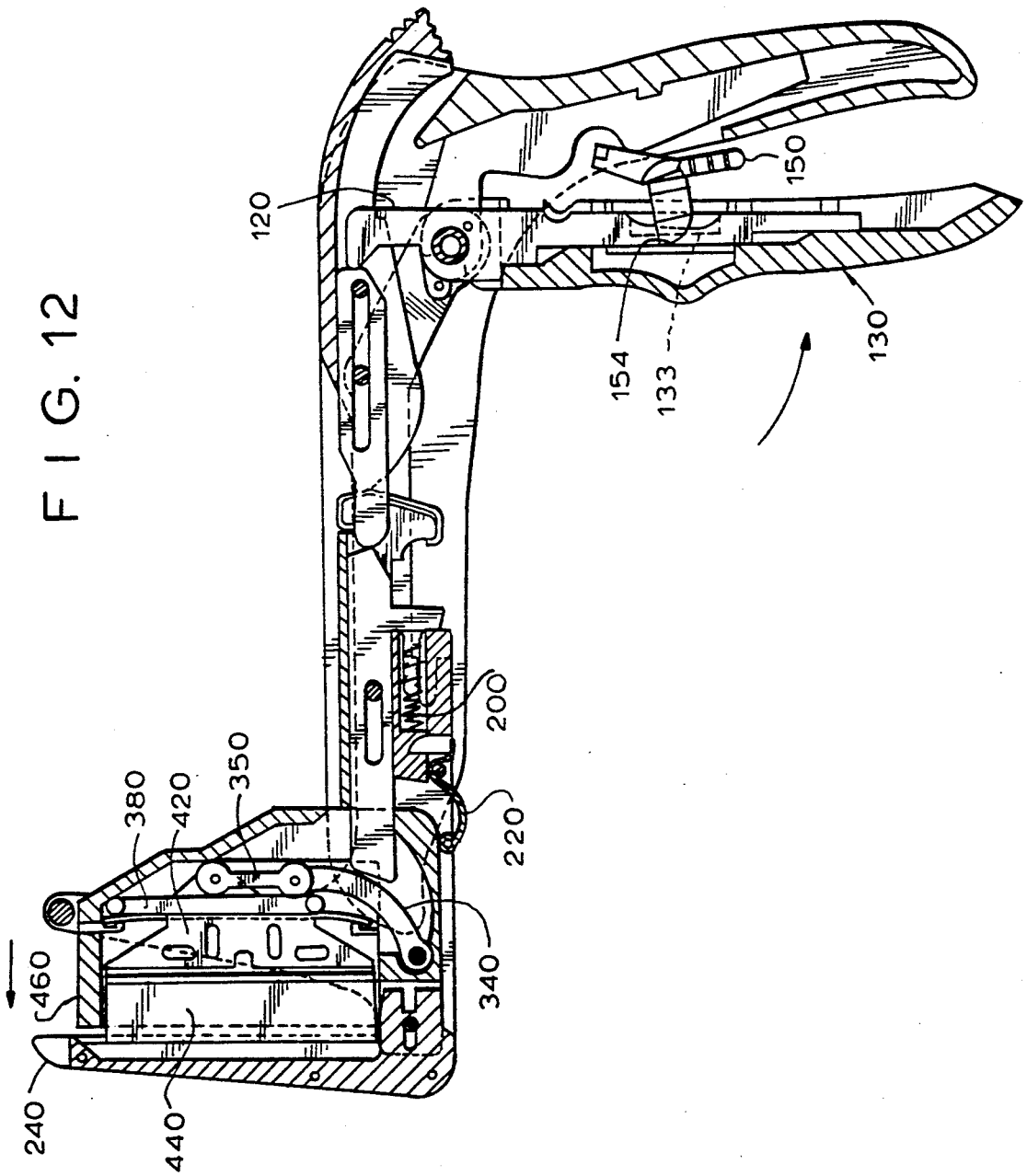

The instrument is now in the fire position illustrated by FIGS. 12 and 15.

Figure 13:
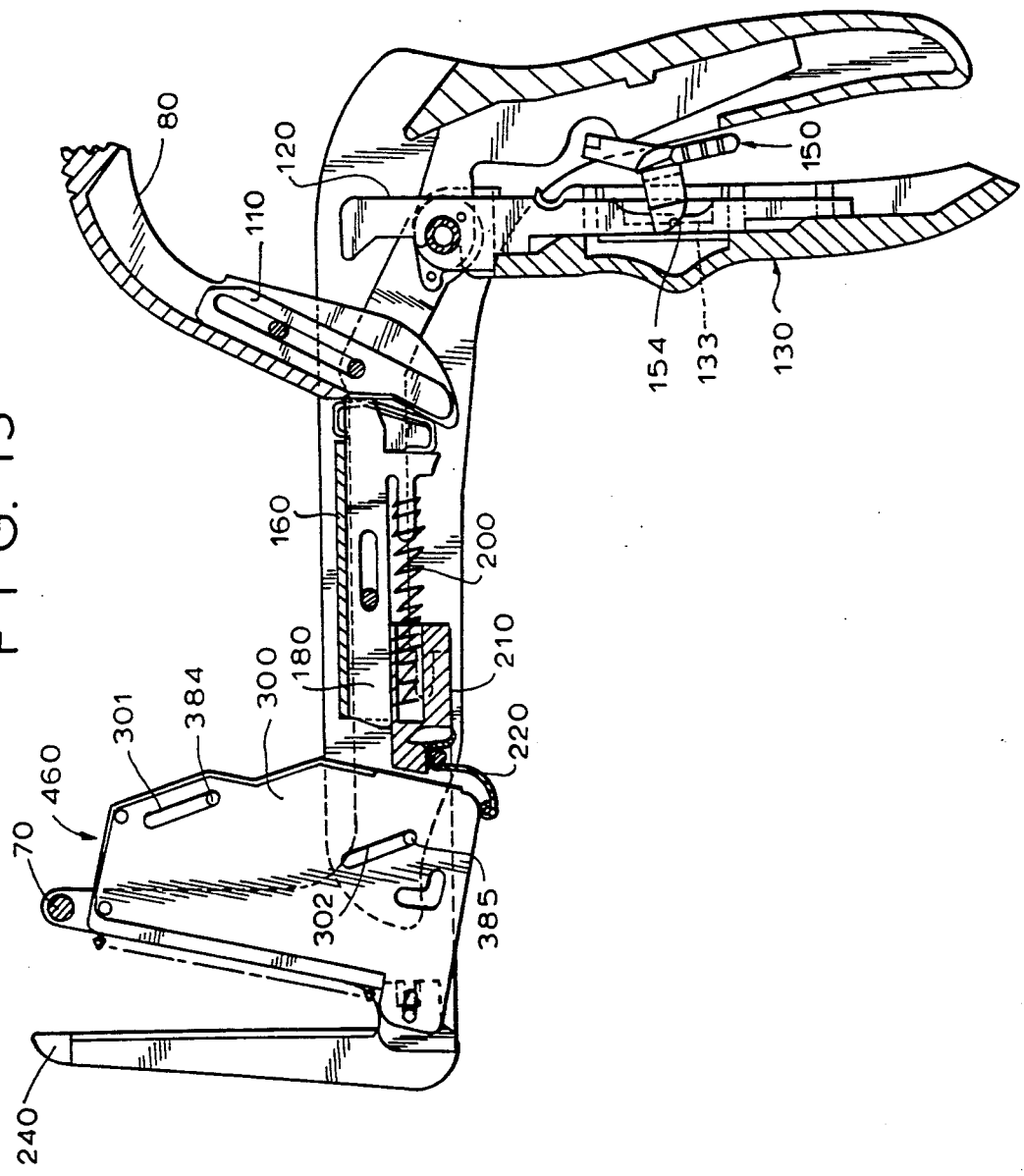

Referring now to FIGS. 13, 15 and 16, to open the instrument and release the body tissue, the surgeon pivots the actuator lever 80 counterclockwise into the upward position as shown in FIG. 13. The knife assembly, being biased proximally by spring 390, retracts into the fastener holder 460. The fastener holder 460 moves back to an open position thereby releasing the body tissue. The thrust bar 180 and clamp 160 return to their proximal position because of the biasing force of spring 20.

The instrument can be made of any size suitable for its purpose of fastening body tissue, and the various parts can be made of materials appropriate to their function. For example, the body, actuator lever, and trigger can be injection molded from a high strength polymer. The frames, cam assembly, fastener pushers, and blade channel can be constructed from an appropriate metal.

The instrument has application in a full range of surgical applications including abdominal, gynecological, pediatric, and thoracic surgery for resection and transection. In a preferred embodiment, the instrument includes bioabsorbable fasteners and retainers and has application in the creation of a temporary opening such as hysterotomy, to align the tissue layers and minimize bleeding during a cesarean delivery.

While the above description contains many specific details, these details should not be construed as limitations on the scope of the invention, but merely as examples of preferred embodiments thereof. Those skilled in the art will envision many other possible variations that are within the scope and spirit of the invention as defined by the claims appended hereto.

What is claimed is:

1. Apparatus for substantially simultaneously applying a plurality of surgical fasteners to body tissue, which comprises a body having a distal end and a proximal end and having a longitudinal portion enclosing axial drive means for transmitting a distally directed drive force, a distal portion of said apparatus including a tissue reception space; anvil means for closing fasteners, said anvil means being positioned at the distal portion of said tissue reception space; fastener holding means for initially holding said surgical fasteners, said fastener holding means being pivotally mounted relative to said anvil means adjacent one end portion thereof and defining said tissue reception space therebetween, said fastener holding means containing a plurality of surgical fasteners arranged in generally parallel rows extending transversely to said longitudinal portion, and said rows being movable distally along respective paths each path having a centerline generally parallel to said longitudinal portion, said centerlines defining a center plane and said longitudinal portion being generally offset from said center plane; means for initially advancing said fastener holding means distally at least sufficient to contact body tissue positioned within said aperture;

actuation means for reception of a proximally directed user applied force and for translating same to distally directed drive force on said axial drive means generally in alignment with said longitudinal portion; means for translating said distally directed drive force to distally directed fastener drive force distributed generally uniformly over the length of the rows of said plurality of fasteners to apply said fasteners to the body tissue.

2. An apparatus for substantially simultaneously applying a plurality of surgical fasteners to body tissue, including a handle; trigger means movable in response to a user applied drive force for transmitting said drive force to an axial drive means, said axial drive means transmitting said drive force distally along a lengthwise path; body means with a longitudinal portion enclosing said axial drive means, said body means including a distal end and a proximal end; a U-shaped distal portion having a distal leg; an anvil assembly positioned at the distal leg of the U-shaped distal portion; a fastener holding cartridge pivotally mounted relative to the anvil assembly and adjacent one end of the anvil assembly thereby defining a gap between them and containing a plurality of surgical fasteners and optionally including knife means for cutting body tissue; the apparatus further including approximation means for actuating the fastener holding cartridge; and fastener pushing means for substantially simultaneously pushing all of the fasteners from the fastener holding cartridge, said fastener pushing means having a proximal end and being linearly movable along a path having an axial centerline of movement in response to drive force applied to said proximal end; and said apparatus being characterized in that:

the lengthwise path of the distally directed drive force transmitted by the drive means is in off-center alignment relative to the axial centerline of movement of the fastener pushing means, and said apparatus further includes means for translating said distally directed drive force to an evenly distributed drive force across the proximal end of said fastener pushing means.

3. The apparatus of claim 2 wherein said means for translating said distally directed drive force comprises:
a movable cam bar having a distal camming surface;
a surface for receiving movement from the off-centered path of said axial drive means;
means including at least one pivotable link for transmitting movement from said axial drive means to the cam bar;
means for maintaining said distal surface of the cam bar in an orientation substantially perpendicular to the centerline of movement of the fastener pushing means; and
means for transferring motion from said distal camming surface to said fastener pushing means.

4. The apparatus of claim 3 wherein said means for maintaining said distal surface of the ca bar in said substantially perpendicular orientation comprises at least one first member which projects from the cam bar and which is fixedly attached thereto, and at least one second member associated with the fastener holding cartridge, said second member having at least one guide surface contacted by said first member for restraining the movement of the first member to a predetermined path.

5. The apparatus of claim 4 wherein said second member is stationary relative to the fastener holder.

6. The apparatus of claim 5 wherein said second member comprises a side plate having a slot defined by said at lest one guide surface.

7. An apparatus for substantially simultaneously applying a plurality of two-part surgical fasteners to body tissue, said two-part surgical fasteners each having a fastener portion and a retainer portion, said apparatus including a handle; a trigger means for receiving a user applied force; a body with a longitudinal portion enclosing an axial drive means for transmitting a drive force along a lengthwise path; a U-shaped distal portion having a distal leg; an anvil assembly for holding the retainers, said anvil assembly being mounted at the distal leg of the U-shaped distal portion; a fastener holding cartridge pivotally mounted relative to the anvil assembly adjacent one end of the anvil assembly thereby defining a gap between them and containing a plurality of fasteners and optionally including a knife means for cutting body tissue; the apparatus further including approximating means for actuating the fastener holding cartridge; and a fastener pushing means for substantially simultaneously pushing all of the fasteners from the fastener holding cartridge; and said apparatus being characterized in that:

the U-shaped distal portion of the apparatus is defined by two U-shaped plate portions of supporting frame means mounted in parallel spaced apart relation to each other and having flat mutually facing surfaces and proximal legs with end portions extending above said fastener holding cartridge, said two U-shaped plate portions being connected by a spacer pin transversely mounted therebetween at the end portions of their respective proximal legs, and said plate portions of the frame means and said spacer pin cooperating so as to align the anvil assembly with the fastener holding cartridge.

8. The apparatus of claim 7, wherein said U-shaped plate portions are fabricated from stainless steel having a thickness of at least 0.07 inches.

9. An apparatus for applying a plurality of surgical fasteners to body tissue, said apparatus having a distal end and a proximal end and comprising:
- a body with a longitudinal portion enclosing an axial drive means for translating a distally directed drive force along a longitudinal path through said body;
- a handle associated with said body;
- a trigger means associated with said body for receiving a user applied force and;
- an anvil assembly;
- a fastener holding cartridge pivotally mounted relative to the anvil assembly adjacent one end of the anvil assembly thereby defining a gap between them, said fastener holding cartridge containing a plurality of surgical fasteners and including a knife means for cutting body tissue, said knife means being distally movable in response to movement of the axial drive means;
- approximating means for actuating the fastener holding cartridge; and
- a fastener pushing means responsive to movement of the drive means for pushing the fasteners from the fastener holding cartridge said fastener pushing means being movable along a path, the centerline of said fastener pushing means path being non-collinear with the centerline of said drive means path;
- means for translating said drive force from said drive means to a force evenly distributed along a proximal surface of said fastener pushing means;
- wherein said knife means possesses a distally facing elongated surface for contacting the proximal end of the fastener pushing means, said distally facing elongated surface of the knife means abutting and moving said fastener pushing means in response to the distal movement of the axial drive means.

10. The apparatus of claim 9 wherein said knife means comprises a knife blade with a distal cutting edge and a proximal edge fixed to a blade holder which is slidably mounted within the fastener holding cartridge, said blade holder having at least one distally facing elongated surface parallel to and on each side of said knife blade.

11. The apparatus of claim 9 wherein said fastener pushing means comprises at least one pusher plate having a plurality of distally projecting flat finger-like projections, each projection being for pushing a respective one of the fasteners from the fastener holder cartridge.

12. An apparatus for applying a plurality of surgical fasteners to body tissue, said apparatus having a distal end and a proximal end and comprising:
- a body with a longitudinal portion enclosing an axial drive means for transmitting a drive force longitudinally through said apparatus;
- a handle associated with said body;
- a trigger means associated with said body for receiving a user applied force;
- an anvil assembly;
- a fastener holding cartridge pivotally mounted relative to the anvil assembly and being adjacent one end of the anvil assembly thereby defining a gap between said fastener holding cartridge and said anvil assembly, said fastener holding cartridge containing a plurality of surgical fasteners and optionally including a knife means for cutting body tissue, said knife means being distally movable in response to movement of the axial drive means;
- approximating means for actuating the fastener holding cartridge; and
- fastener pushing means for pushing the fasteners from the fastener holding cartridge, said fastener pushing means including a pusher plate movable from a proximal position to a distal position in response to movement of the axial drive means and which is substantially flat on two opposite sides and which has a plurality of fastener-pushing members distally projecting from a back portion and interference means associated with at least one of the flat sides for frictionally engaging a cooperating surface of the fastener holding cartridge to prevent the fastener pusher plate from moving proximally after said plate has been moved to said distal position in response to movement of the axial drive means, said fastener pushing means having a centerline of movement non-collinear with said axial drive means; and
- directing means for converting the drive force transmitted by said axial drive means to a drive force evenly distributed to the fastener pushing means.

13. The apparatus of claim 12 wherein said interference means comprises at least one detent projecting from the side of said pusher plate.

14. A fastener holding cartridge for use in an instrument for applying a plurality of surgical fasteners, which comprises:
- a housing having a distal end and proximal end and containing a plurality of surgical fasteners, each fastener being slidably mounted within a slot;
- fastener pushing means which is movable in a path having a centerline of movement for linearly pushing said fasteners from their respective slots in response to application of an off-centered linear drive force provided by drive means which is movable in a linear path which is non-collinear with the centerline of movement of the fastener pushing means;
- redirecting means for converting the off-centered drive force to a drive force evenly distributed to the fastener pushing means, said redirecting means including a surface for receiving the off-centered drive force, a means for transmitting said force to a cam bar, said cam bar having a substantially flat distal surface for contacting the fastener pushing means and having a path of movement with a vector component aligned with the path of movement of the fastener pushing means, and said redirecting means further including means for restraining the orientation and movement of the cam bar such that the distal surface of the cam bar remains perpendicular relative to the centerline of movement of the fastener pushing means.

15. The fastener holding cartridge of claim 14 wherein said fastener pushing means comprises at least one pusher plate having a plurality of distally projecting, flat, finger-like projections, each projection being for pushing a respective one of the fasteners from said fastener holding cartridge.

16. The fastener holding cartridge of claim 15 wherein said pusher plate is movable from a proximal position to a distal position and has interference means for frictionally engaging a cooperating surface of the fastener holding cartridge when said pusher plate is in said distal position to prevent said pusher plate from returning to its proximal position.

17. The fastener holding cartridge of claim 16 wherein said interference means comprises at least one detent projecting from at least one of said pusher plate.

18. The fastener holding cartridge of claim 14 further comprising a knife means for cutting body tissue, said knife means being movable between a proximal position in which said knife means is completely enclosed by said cartridge and a distal position wherein a cutting edge of said knife means projects out of a corresponding slot in the distal end of the cartridge, said movement of the knife means being in response to movement of said linear drive force.

19. The fastener holding cartridge of claim 18 further including resilient means for biasing said knife means to its proximal position.

20. The fastener holding cartridge of claim 19 wherein said resilient means comprises a leaf spring.

21. The fastener holding cartridge of claim 14 wherein said means for restraining the orientation and movement of the cam bar comprises at least one first member which projects from the cam bar and is fixedly attached thereto, and at least one second member which is associated with the fastener holding cartridge, said second member having at least one guide slot for receiving said first member and for restraining its movement to a predetermined path.

22. The fastener holding cartridge of claim 21 wherein said second member is stationary relative to the fastener holding cartridge.

23. The fastener holding cartridge of claim 22 wherein said second member is a side plate.

* * * * *